United States Patent
Liu et al.

(10) Patent No.: US 11,953,455 B1
(45) Date of Patent: Apr. 9, 2024

(54) ORE COMPONENT ANALYSIS DEVICE AND METHOD

(71) Applicants: SHANDONG UNIVERSITY, Weihai (CN); WEIHAI RESEARCH INSTITUTE OF INDUSTRIAL TECHNOLOGY OF SHANDONG UNIVERSITY, Weihai (CN)

(72) Inventors: Chen Liu, Weihai (CN); Shouyu Wang, Weihai (CN)

(73) Assignee: SHANDONG UNIVERSITY, Weihai (CN)

( * ) Notice: Subject to any disclaimer, the term of this patent is extended or adjusted under 35 U.S.C. 154(b) by 0 days.

(21) Appl. No.: 18/401,182

(22) Filed: Dec. 29, 2023

Related U.S. Application Data

(63) Continuation-in-part of application No. PCT/CN2023/072483, filed on Jan. 17, 2023.

(51) Int. Cl.
*G01N 23/223* (2006.01)
*G01N 33/24* (2006.01)

(52) U.S. Cl.
CPC ........... *G01N 23/223* (2013.01); *G01N 33/24* (2013.01); *G01N 2223/076* (2013.01); *G01N 2223/1016* (2013.01); *G01N 2223/206* (2013.01); *G01N 2223/303* (2013.01); *G01N 2223/3037* (2013.01); *G01N 2223/304* (2013.01); *G01N 2223/309* (2013.01); *G01N 2223/3306* (2013.01); *G01N 2223/616* (2013.01)

(58) Field of Classification Search
None
See application file for complete search history.

(56) References Cited

U.S. PATENT DOCUMENTS

| 6,130,931 A | 10/2000 | Laurila |
| 7,627,088 B2 * | 12/2009 | Matoba ................. H01J 35/186 378/45 |

(Continued)

FOREIGN PATENT DOCUMENTS

| CN | 101355002 A | 1/2009 |
| CN | 103278485 A | 9/2013 |

(Continued)

OTHER PUBLICATIONS

Machine translation of JP H07-190961 A. (Year: 1995).*
International Search Report for PCT/CN2023/072483.

*Primary Examiner* — Thomas R Artman
(74) *Attorney, Agent, or Firm* — J.C. PATENTS

(57) ABSTRACT

An ore component analysis device and method are provided, the analysis device comprises: a sample containing device configured to place an ore sample to be detected; an excitation unit configured to output X-rays with continuously adjustable energy; a detector configured to detect the secondary X-rays; a signal processing unit configured to amplify, shape and classify the secondary X-rays to obtain counts and energy of the secondary X-rays; a data processing device comprising a processor configured to execute a storage module, a matching module, a count correction module, a peak seeking module, a calculation module and a content correction module stored in a memory, so as to obtain elements and contents thereof in the ore sample. The present application can be directly applied to production line for qualitative and quantitative analysis of ore components.

15 Claims, 3 Drawing Sheets

(56) References Cited

U.S. PATENT DOCUMENTS

| | | | |
|---|---|---|---|
| 7,796,726 B1 | 9/2010 | Gendreau | |
| 10,697,953 B2* | 6/2020 | Weindorf | G01N 33/246 |
| 10,900,946 B2* | 1/2021 | Weindorf | G01N 21/274 |
| 10,900,947 B2* | 1/2021 | Weindorf | G01N 23/223 |
| 11,340,207 B2* | 5/2022 | Rocher | G01N 23/2206 |
| 11,782,000 B2* | 10/2023 | Kataoka | G01N 23/2208 |
| | | | 378/44 |
| 11,821,857 B2* | 11/2023 | Krumm | G01N 1/286 |
| 2009/0028297 A1* | 1/2009 | Matoba | H01J 35/186 |
| | | | 378/207 |
| 2011/0007869 A1* | 1/2011 | Gendreau | G01N 23/20 |
| | | | 378/46 |
| 2019/0049423 A1* | 2/2019 | Weindorf | G01N 23/223 |
| 2019/0056374 A1* | 2/2019 | Rocher | G01N 23/207 |
| 2020/0141917 A1* | 5/2020 | Weindorf | G01N 23/223 |
| 2020/0232964 A1* | 7/2020 | Weindorf | G01N 33/246 |
| 2021/0244374 A1 | 8/2021 | Zhao | |
| 2022/0107279 A1* | 4/2022 | Krumm | G01N 33/24 |
| 2022/0317069 A1* | 10/2022 | Grof | G01N 33/381 |
| 2023/0060446 A1* | 3/2023 | Kataoka | G01N 23/2208 |

FOREIGN PATENT DOCUMENTS

| | | | |
|---|---|---|---|
| CN | 112213342 A | | 1/2021 |
| CN | 113155809 A | | 7/2021 |
| CN | 115763616 A | | 3/2023 |
| CN | 116297602 A | | 6/2023 |
| JP | H07190961 A | * | 7/1995 |

\* cited by examiner

ORE COMPONENT ANALYSIS DEVICE AND METHOD

CROSS-REFERENCE TO RELATED APPLICATION

This application is a continuation-in-part application of the international application PCT/CN2023/072483 filed on Jan. 17, 2023, the content of which is herein incorporated by reference in its entirety.

TECHNICAL FIELD

The present application belongs to the technical field of component analysis, and relates to the technology of ore component analysis, in particular to an ore component analysis device and method.

BACKGROUND ART

The mining industry is a pillar industry in national economy. With the rise of new technologies such as 5G network, big data, artificial intelligence and cloud computing, intelligence, as a disruptive and innovative technology, has become the core driving force for the transformation of basic industries worldwide. The use of intelligent high-tech to promote the transformation and upgrading of the traditional mining industry can essentially enhance the core competitiveness of mine enterprises. Mining intelligence involves mine geology, surveying, mining, ore dressing, safety and other links, among which the intelligence of ore screening and processing is an important link and a critical point of mining intelligence. It is well known that the determination of ore-rock components is very important for mine production planning, mining, ore blending, etc. Due to long period, low efficiency and other reasons, the traditional ore-rock determination methods by field sampling and laboratory test have become the bottleneck in the construction of intelligence mine. How to develop new ore-rock component analysis device to meet the requirements of mining development in the new era is a problem to be solved urgently and is also the key to the construction of intelligence mine.

The component analysis technology is mainly used to analyze unknown objects and unknown components of minerals. By the component analysis technology, various constituent elements in the target sample can be quickly determined, and the sample can be quickly analyzed qualitatively and quantitatively. In recent years, as an important branch of the component analysis technology, the X-ray fluorescence analysis technology has developed rapidly. Nowadays, the energy dispersive X-ray fluorescence (EDXRF) analysis technology has developed as a comprehensive technology integrating many advanced technologies, including electronic technology, data analysis, nuclear physics and computer technology. Since EDXRF has entered the analysis instrument industry, due to its advantages of no damage to samples, high accuracy of analysis results, reliability of data analysis and the like, EDXRF has been more and more widely applied in mineral exploration, aerospace, geological exploration, petrochemical industry and other fields. Especially since July, 2016, the European Union began to implement the RoHS directive, and the demand for EDXRF analyzers in the market increased sharply. Therefore, the development of EDXRF spectrometers has important scientific significance and market value.

However, the existing XRF analyzers in the market are basically used for laboratory data analysis, cannot intuitively give the proportion of each element in the sample in the mining and production process, and have complicated maintenance and tedious operation process. Moreover, the process of "sampling-sample presentation-laboratory test-result feedback to the production line" will take about 2 weeks, which greatly wastes manpower and time cost. In addition, the existing XRF analyzers are too specialized and cannot directly operate on the production line, so that it is disadvantageous for industrial scale production and intelligent application.

SUMMARY OF THE PRESENT INVENTION

In view of at least one of the above deficiencies of the existing component analysis devices, the present application provides an ore component analysis device and method.

According to one aspect of the present application, an ore component analysis device is provided, comprising:

a sample containing device, which is configured to place an ore sample to be detected;

an excitation unit, which is arranged above the sample containing device and configured to output X-rays with continuously adjustable energy, so that the X-rays interact with the ore sample to be detected and excite the ore sample to generate secondary X-rays;

a detector, which is arranged above the sample containing device and configured to detect the secondary X-rays;

a signal processing unit, which is connected to the detector and configured to amplify, shape and classify the secondary X-rays detected by the detector to obtain counts and energy of the secondary X-rays; and a data processing device, which is connected to the signal processing unit and configured to analyze and calculate data processed by the signal processing unit, wherein the data processing device comprises a processor and a memory, and the processor is configured to execute following program modules stored in the memory:

a storage module, which is configured to store known elements and energy and occurrence probability of X-rays corresponding to the elements;

a matching module, which is configured to match the energy of the secondary X-rays with the energy of the X-rays corresponding to the known elements stored in the storage module so as to determine elements corresponding to the secondary X-rays and obtain occurrence probability of the secondary X-rays;

a count correction module, which is configured to correct the counts of the secondary X-rays according to attenuation efficiency of the secondary X-rays in the air to obtain a corrected energy spectrum of the secondary X-rays;

a peak seeking module, which seeks peaks on the corrected energy spectrum of the secondary X-rays and calculates peak area of each peak;

a calculation module, which calculates content of each element in the ore sample according to the peak area and the occurrence probability of the secondary X-rays, where the content $P_i$ of an element i is expressed as:

$$P_i = \frac{I_i}{\sum I_i} = \frac{A_i/(\varepsilon_i \times \varepsilon_j)}{\sum A_i/(\varepsilon_i \times \varepsilon_j)}, \tag{1}$$

where $I_i$ is an intensity of the element i, $A_i$ is the peak area of the element i, $\varepsilon_i$ is the occurrence probability of the secondary X-rays of the element i, and $\varepsilon_j$ is intrinsic detection efficiency of the detector for the secondary X-rays of the element i; and a content correction module, which is configured to perform matrix effect correction on the content of each element calculated by the calculation module by using a measurement result of a standard ore sample to obtain final content of each element in the ore sample.

In some embodiments of the present application, an included angle formed by the excitation unit, the sample containing device and the detector is 45° to 135°.

In some embodiments of the present application, the processor is further configured to execute a display module and an Internet of Things module stored in the memory; the display module and the Internet of Things module are connected to the content correction module, respectively; the display module is configured to display the final content of each element in the ore sample; and, the Internet of Things module is configured for connection to an external data monitoring platform.

In some embodiments of the present application, the sample containing device comprises:
  a rotating member, above which the excitation unit and the detector are located;
  a sample container, which is placed in the rotating member and configured to place the ore sample to be detected; and
  a driving member, having an output shaft which is coupled to a bottom of the rotating member and configured to drive the rotating member to rotate.

In some embodiments of the present application, the processor is further configured to execute a control module stored in the memory; the control module is connected to the driving member and configured to control the driving member to drive the rotating member rotate at a set angle α every set time T, so that the detector performs multi-point detection on the ore sample to be detected to obtain an average value.

In some embodiments of the present application, the excitation unit comprises:
  a high-voltage power source, which is configured to output high-voltage power with different voltages; and
  a controllable X-ray excitation source, which is electrically connected to the high-voltage power source and configured to output the X-rays with continuously adjustable energy according to the different voltages output by the high-voltage power source, so that the X-rays interact with the ore sample to be detected and excite the ore sample to generate the secondary X-rays.

In some embodiments of the present application, the signal processing unit comprises:
  a signal amplifier, which is connected to the detector and configured to amplify and shape the secondary X-rays detected by the detector; and
  a multichannel pulse amplitude analyzer, which is connected to the signal amplifier and configured to perform analog-to-digital conversion on amplified secondary X-rays and then perform classification to obtain the counts and the energy of the secondary X-rays.

In some embodiments of the present application, a specific method of correcting the counts of the secondary X-rays by the count correction module is given as follows: assuming that the energy of the secondary X-rays is E, a corrected count of the secondary X-rays with energy of E is expressed as:

$$y = x/\varepsilon 1 \qquad (2),$$

where y denotes the corrected count of the secondary X-rays, x denotes a count of the secondary X-rays with energy of E, and ε1 denotes the attenuation efficiency of the secondary X-rays with energy of E in 1 cm air and measured by experiments.

In some embodiments of the present application, a specific step of performing matrix effect correction by the content correction module is given as follows: assuming that content of the element i in the standard ore sample is A and content of the element i in the standard ore sample calculated by the calculation module is B, then the final content $P_{ALi}$ of the element i in the ore sample to be detected is:

$$P_{ALi} = \frac{P_i}{B/A}. \qquad (3)$$

According to a second aspect of the embodiments of the present application, an ore component analysis method is provided, which performs analysis by using the ore component analysis device according to any one of the aforementioned embodiments, the analysis method comprising following steps of:

S1: emitting X-rays with continuously adjustable energy to an ore sample to be detected, so that the X-rays with different energy interact with the ore sample to be detected and excite the ore sample to generate secondary X-rays with different energy;

S2: detecting the secondary X-rays, amplifying, shaping and classifying the secondary X-rays to obtain counts and energy of the secondary X-rays with different energy;

S3: matching the energy of the secondary X-rays with energy of X-rays corresponding to known elements to determine elements corresponding to the secondary X-rays and obtain occurrence probability of the secondary X-rays;

S4: correcting the counts of the secondary X-rays according to attenuation efficiency of the secondary X-rays in the air to obtain a corrected energy spectrum of the secondary X-rays, seeking peaks on the corrected energy spectrum of the secondary X-rays, and calculating peak area of each peak;

S5: calculating content of each element in the ore sample according to the peak area and the occurrence probability of the secondary X-rays, where the content $P_i$ of an element i is expressed as:

$$P_i = \frac{I_i}{\sum I_i} = \frac{A_i/(\varepsilon_i \times \varepsilon_j)}{\sum A_i/(\varepsilon_i \times \varepsilon_j)}, \qquad (1)$$

where $I_i$ is an intensity of the element i, $A_i$ is the peak area of the element i, $\varepsilon_i$ is the occurrence probability of the secondary X-rays of the element i, and $\varepsilon_j$ is intrinsic detection efficiency of the detector for the secondary X-rays of the element i and the content of each element is calculated according to the above formula;

S6: performing matrix effect correction on the calculated content of each element by using a measurement result of a standard ore sample to obtain final content of each element in the ore sample.

In some embodiments of the present application, an excitation unit and a detector are arranged above the ore sample to be detected; the X-rays are output by the excitation unit, and the secondary X-rays are detected by the detector; and, an included angle formed by the excitation unit, the sample containing device and the detector is 45° to 135°.

In some embodiments of the present application, in the step S4, a specific method of correcting the counts of the secondary X-rays is given as follows: assuming that the energy of the secondary X-rays is E, a corrected count of the secondary X-rays with energy of E is expressed as:

$$y = x/\varepsilon 1 \qquad (2),$$

where y denotes the corrected count of the secondary X-rays, x denotes a count of the secondary X-rays with energy of E, and $\varepsilon_1$ denotes the attenuation efficiency of the secondary X-rays with energy of E in 1 cm air and measured by experiments.

In some embodiments of the present application, a specific step of performing matrix effect correction is given as follows: assuming that content of the element i in the standard ore sample is A and content of the element i in the standard ore sample calculated by the formula (1) is B, then the final content $P_{ALi}$ of the element i in the ore sample to be detected is:

$$P_{ALi} = \frac{P_i}{B/A}. \qquad (3)$$

In some embodiments of the present application, in the step S1, multi-angle measurement of the ore sample is realized by changing an angle of the ore sample to be detected.

In some embodiments of the present application, after the step S6, the method further comprises a step S7: displaying elements in the ore sample and the content of each element and uploading to an external data monitoring platform.

Compared with the prior art, the present application has the following advantages and positive effects.

(1) In the ore component analysis device provided in at least one embodiment of the present application, a count correction module is provided to correct the counts of the secondary X-rays according to the attenuation efficiency of the X-rays in the air, and a content correction module is provided to perform matrix effect correction on the calculated content of each element by using the measurement result of the standard ore sample, so that the analysis device can be directly used in the air without the control of the vacuum pump and can be directly applied to the production line to obtain the mineral composition and the content information of each element, thereby simplifying the ore component analysis process.

(2) In the ore component analysis device provided in at least one embodiment of the present application, the relative positions of the X-ray excitation source, the ore sample and the detector are limited, and the X-ray excitation source and the detector are arranged at an angle of 45° to 135°, so that it can be ensured that the ore sample to be detected is effectively excited by the X-rays, and the excited secondary X-rays can be fully absorbed by the detector.

(3) In the ore component analysis device provided in at least one embodiment of the present application, the sample containing device is designed independently and comprises a rotating member, a sample container placed in the rotating member and a driving member connected to the rotating member. By driving the rotating member to rotate by the driving member, the sample container can rotate at a certain angle every certain time, and multi-point measurement is performed on the ore sample to be detected to obtain an average value, so that the measurement deviation caused by uneven distribution of elements inside the sample is solved and the measurement result is more accurate.

(4) In the ore component analysis device provided in at least one embodiment of the present application, a display device and an Internet of Things module are also provided. The display device can display the analyzed elements in the ore and the content value of each element, and the Internet of Things module can transmit the analyzed elements in the ore and the content value of each element to an external data monitoring platform (e.g., our own cloud platform, a third-party platform, etc.). Thus, according to the component analysis result, the control of ore classification/desliming and other operations is realized, the current production mode of the ore processing industry is changed, and the production efficiency is improved.

(5) In the ore component analysis device provided in at least one embodiment of the present application, the counts of the secondary X-rays is corrected according to the attenuation efficiency of the X-rays in the air, and matrix effect correction is performed on the calculated content of each element by using the measurement result of the standard ore sample, so that the ore component analysis can be directly used in the air without the control of the vacuum pump and can be directly applied to the production line, thereby simplifying the ore component analysis process.

in which: 1: sample containing device; 11: supporting surface; 101: rotating member; 102: sample container; 103: driving member; 2: excitation unit; 201: high-voltage power source; 202: controllable X-ray excitation source; 3: detector; 31: detection surface; 4: signal processing unit; 401: signal amplifier; 402: multichannel pulse amplitude analyzer; 5: data processing device; 501: processor; 502: memory; 51: storage module; 52: matching module; 53: count correction module; 54: peak seeking module; 55: calculation module; 56: content correction module; 57: display module; 58: Internet of Things module; 59: control module; and, 6: external data monitoring platform.

DETAILED DESCRIPTION OF THE PRESENT INVENTION

The present application will be specifically described below by exemplary implementations. However, it should be understood that elements, structures and features in one implementation can be advantageously incorporated into other implementations without further recitation.

The embodiments of the present application provide an ore component analysis device and method, which corrects counts of the secondary X-rays according to attenuation efficiency of X-rays in the air and performs matrix effect correction on the calculated content of each element by using a measurement result of a standard ore sample, so that the ore component analysis can be performed without the control of the vacuum pump and can be directly applied to the production line, non-destructive measurement of ore is realized. The ore component analysis device and method will be described below in detail with reference to specific embodiments. In the following description, it is to be noted that the element i only refers to a certain element in the ore sample to be detected, instead of referring to any specific element.

Figure 1:
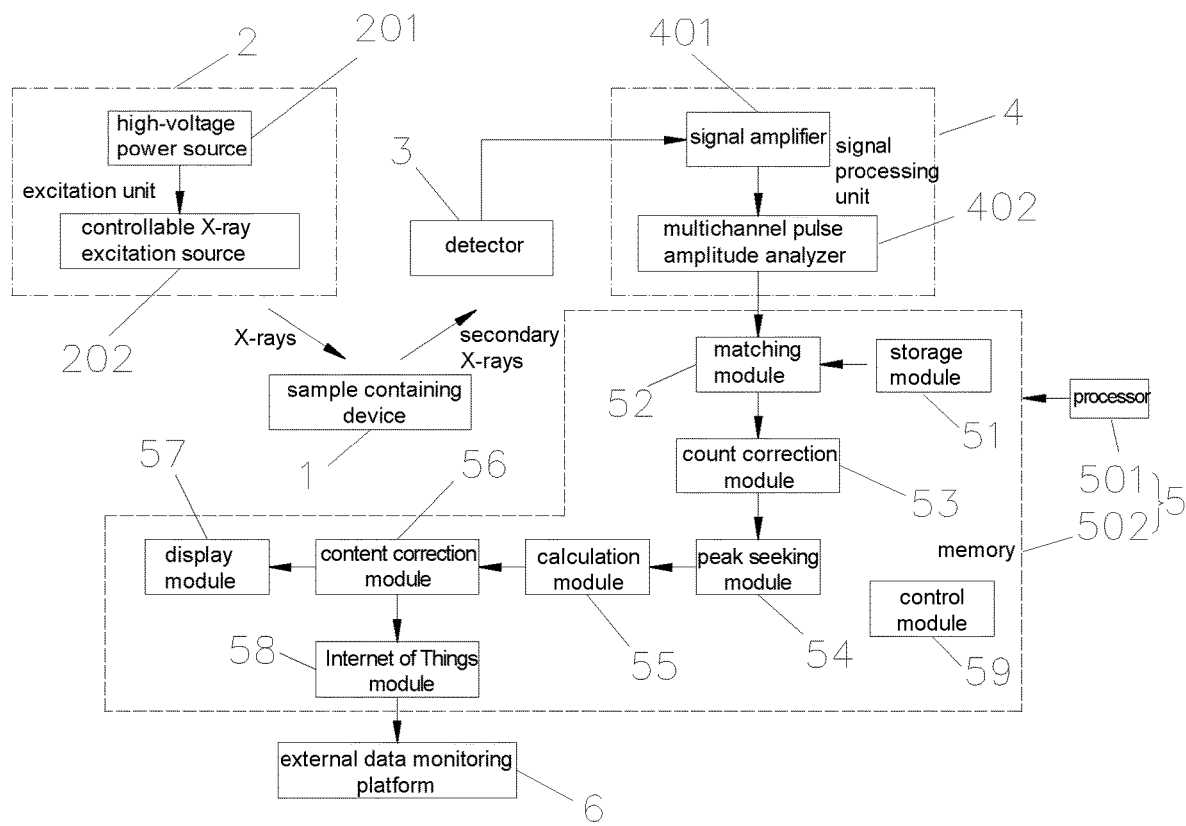
FIG. 1 is a structural block diagram of an ore component analysis device according to an embodiment of the present application.
Figure 2:
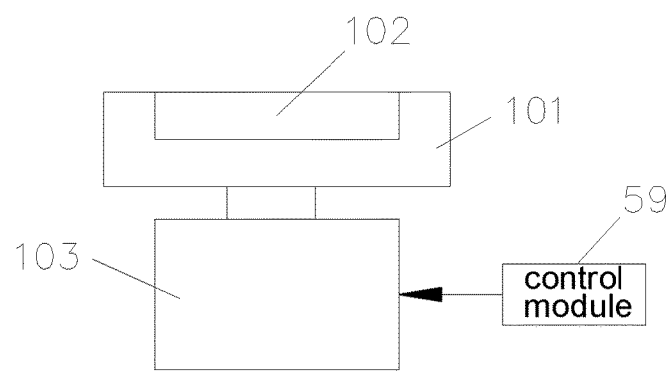
FIG. 2 is a structural schematic diagram of a sample containing device according to an embodiment of the present application.
Figure 3:
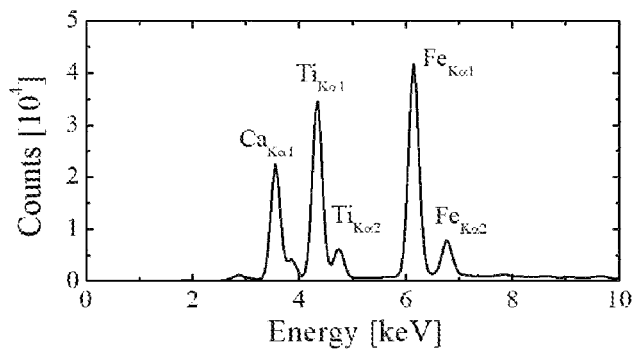
FIG. 3 is a schematic diagram of known elements and the X-ray energy corresponding to the elements.
Figure 4:
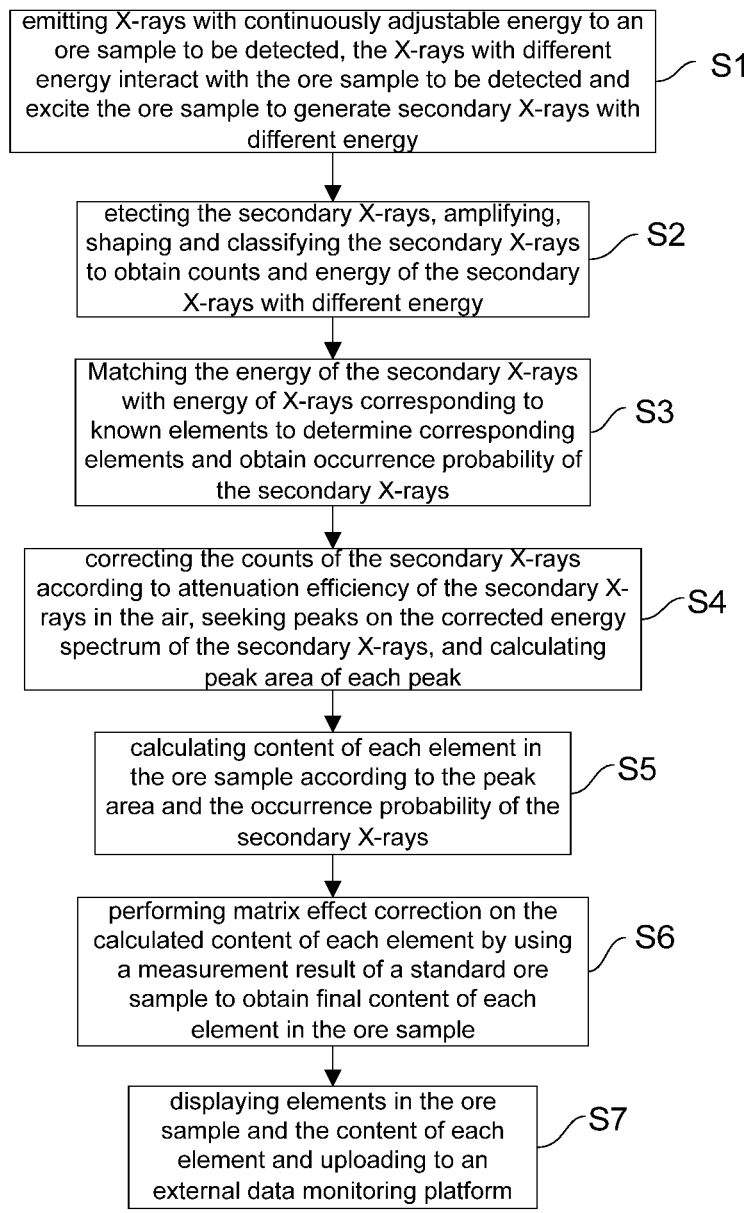
FIG. 4 is a flowchart of an ore component analysis method according to an embodiment of the present application.

According to a first aspect of the embodiments of the present application, an ore component analysis device is provided. As shown in FIG. 1, the device comprises:

a sample containing device 1, which is configured to place an ore sample to be detected;

an excitation unit 2, which is arranged above the sample containing device 1 and configured to output X-rays with continuously adjustable energy, so that the X-rays interact with the ore sample to be detected and excite the ore sample to generate secondary X-rays;

a detector 3, which is arranged above the sample containing device 1 and configured to detect the secondary X-rays;

a signal processing unit 4, which is connected to the detector 3 and configured to amplify, shape and classify the secondary X-rays detected by the detector 3 to obtain counts and energy of the secondary X-rays; and a data processing device 5, which is connected to the signal processing unit 4 and configured to analyze and calculate data (specially, the counts and the energy of the secondary X-rays) processed by the signal processing unit 4, wherein the data processing device 5 comprises a processor 501 and a memory 502, and the processor 501 is configured to execute following program modules stored in the memory 502:

a storage module 51, which is configured to store known elements in ore and energy (for example, referring to FIG. 3 which shows the energy of X-rays corresponding to some elements) and occurrence probability of X-rays corresponding to the known elements;

a matching module 52, which is configured to match the energy of the secondary X-rays output by the signal processing unit 4 with the energy of the X-rays corresponding to the known elements stored in the storage module 51 so as to determine elements corresponding to the secondary X-rays and obtain occurrence probability of the secondary X-rays;

a count correction module 53, which is configured to correct the counts of the secondary X-rays according to attenuation efficiency of the secondary X-rays in the air to obtain a corrected energy spectrum of the secondary X-rays, where a horizontal ordinate of the corrected energy spectrum is the energy of the secondary X-rays, while a vertical ordinate of the corrected energy spectrum is corrected counts of the secondary X-rays;

a peak seeking module 54, which seeks peaks on the corrected energy spectrum of the secondary X-rays and calculates peak area of each peak;

a calculation module 55, which calculates content of each element in the ore sample according to the peak area and the occurrence probability of the secondary X-rays, where the content $P_i$ of an element i is expressed as:

$$P_i = \frac{I_i}{\sum I_i} = \frac{A_i/(\varepsilon_i \times \varepsilon_j)}{\sum A_i/(\varepsilon_i \times \varepsilon_j)}, \qquad (1)$$

where $I_i$ is an intensity of the element i, $A_i$ is the peak area of the element i, $\varepsilon_i$ is the occurrence probability of the secondary X-rays of the element i, $\varepsilon_j$ is intrinsic detection efficiency of the detector for the secondary X-rays of the element i, and unit of $P_i$ is %, wherein, here, $I_i$ can be interpreted as the number of the element i, and the content $P_i$ of the element i in the formula (1) is obtained by dividing the number of the element i by the number of all elements; and a content correction module 56, which is configured to perform matrix effect correction on the content of each element calculated by the calculation module 55 by using a measurement result of a standard ore sample to obtain final content of each element in the ore sample.

It is to be noted that the intrinsic detection efficiency of the detector 3 is a known parameter of the detector 3.

Figure 5:
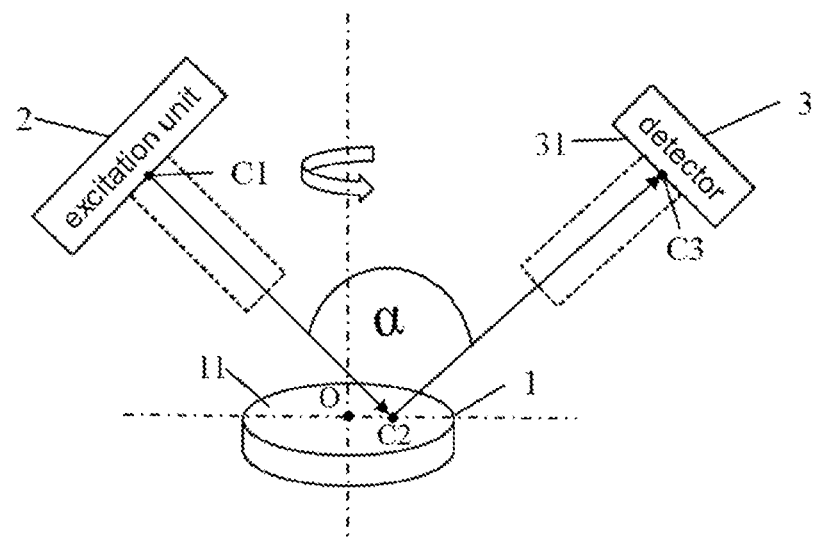
FIG. 5 is a schematic diagram of an included angle α formed by an excitation unit, a sample containing device and a detector in an embodiment of the present application.

In some embodiments, an included angle α formed by the excitation unit 2, the sample containing device 1 and the detector 3 is 45° to 135°. As shown in FIG. 5, an X-ray output port of the excitation unit 2 is marked as point C1 the sample containing device 1 comprises a supporting surface 11 on which the ore sample to be detected is held, a point C2 deviating from a center point O of the supporting surface 11 is taken on the supporting surface 11 and serves as an incident point of X-rays irradiation on the ore sample; the detector 3 comprises a detection surface 31 for receiving the secondary X-rays, and a center point of the detection surface 31 is point C3; the included angle α is formed by a straight line connecting the points C1 and C2 and a straight line connecting the points C2 and C3. When detecting, the supporting surface 11 is covered with the ore sample to be detected, and the X-rays irradiates point C2, since point C2 is deviated from the center point O of the supporting surface 11, when the supporting surface 11 rotates around the center point O, positions where the surface of the ore sample is irradiated by X-rays form a circular ring with the center point O as the center. Specifically, the point C2 can be located at ⅓, ½ or ⅔ of a straight line connecting the center point O and the edge of the supporting surface 11, which can be determined according to requirements. The included angle α can be selected according to actual needs. For example, the included angle α may be 45°, 135°, 60°, 90°, 120°, etc., and may be adjusted by changing the position of the detector 3 and the X-ray output port of the excitation unit 2. By arranging the detector 3 and the excitation unit 2 at the above angle, it can be ensured that the ore sample to be detected can be effectively excited by the X-rays, and the excited secondary X-rays can be fully absorbed by the detector 3.

In some embodiments, a specific method of correcting the counts of the secondary X-rays by the count correction module 53 is given as follows: assuming that the energy of the secondary X-rays is E, a corrected count of the secondary X-rays with energy of E is expressed as:

$$y = x/\varepsilon 1 \qquad (2),$$

where y denotes the corrected count of the secondary X-rays, x denotes a count of the secondary X-rays with energy of E, and $\varepsilon_1$ denotes the attenuation efficiency of the secondary X-rays with energy of E in 1 cm air and can be measured by experiments.

In some embodiments, after peaks are sought on the corrected energy spectrum of the secondary X-rays, the peak area of each peak is calculated by integration. Since it is a known technology to calculate the peak area on the energy spectrum by integration, the specific process of calculating the peak area by integration will not be described in detail here.

In some embodiments, a specific step of performing matrix effect correction by the content correction module 56 is given as follows: assuming that content of the element i in the standard ore sample is A and content of the element i in the standard ore sample calculated by the calculation module is B, then the final content $P_{ALi}$ of the element i in the ore sample to be detected is:

$$P_{ALi} = \frac{P_i}{B/A}. \quad (3)$$

For example, if a concentration of element potassium in the standard ore sample is 10% and a concentration of element potassium in the standard ore sample calculated by the calculation module is 15% which is 1.5 times of the real concentration, during the measurement of a non-standard sample, the final content of element potassium in the non-standard sample is obtained by dividing the calculated content $P_K$ by 1.5. If a concentration of element calcium in the standard ore sample is 10% and a concentration of element calcium in the standard ore sample calculated by the calculation module is 13% which is 1.3 times of the real concentration, during the measurement of a non-standard sample, the final content of element calcium in the non-standard sample is obtained by dividing the calculated content $P_{Ca}$ by 1.3.

In some embodiments, the processor 502 is further configured to execute a display module 57 and an Internet of Things module 58 stored in the memory 502, the display module 57 and the Internet of Things module 58 are connected to the content correction module 56, respectively; the display module 57 is configured to display the final content of each element in the ore sample, and the Internet of Things module 58 is configured for connection to an external data monitoring platform 6. The display module 57 can display the analyzed elements in the ore and the content value of each element, and the Internet of Things module 58 can transmit the analyzed elements in the ore and the content value of each element to the external data monitoring platform (e.g., our own cloud platform, a third-party platform, etc.). Thus, according to the component analysis result, the control of ore classification/desliming and other operations is realized, and the automatic control in the ore processing process is also realized, thus the current production mode of the ore processing industry is changed, and the production efficiency is improved.

In some embodiments, the data processing device 5 specifically adopts an upper computer. The processor 501 and the memory 502 are configured in the upper computer, and the storage module 51, the matching module 52, the count correction module 53, the peak seeking module 54, the calculation module 55, the content correction module 56, the display module 57 and the Internet of Things module 58 are stored in the memory 502.

In some embodiments, the sample containing device 1 is a sample cup or a sample tray.

In other embodiments, the sample containing device 1 comprises: a rotating member 101, above which the excitation unit 2 and the detector 3 are located; a sample container 102, which is placed in the rotating member 101; and, a driving member 103, having an output shaft which is coupled to a bottom of the rotating member 101 and can drive the rotating member to rotate. Optionally, the sample container 102 is a sample cup or a sample tray, the rotating member 101 is a lead box, and the driving member 103 is a motor.

By using the sample containing device provided in the above embodiment, the rotating member 101 is driven to rotate by the driving member 103, and the sample in the sample container 102 also rotates together with the rotating member 101, so that multi-point measurement can be performed on the sample to obtain an average value, the measurement deviation caused by uneven distribution of elements inside the sample is solved, and the measurement result is more accurate.

It is also to be noted that the rotating member 101 adopts a lead box. During measurement, the lead box keeps rotating so that the ore sample in the lead box can be uniformly excited, and the average value of the content of the whole batch of samples can be finally obtained, thereby reducing the error.

In some embodiments, the processor 501 is further configured to execute a control module 59 stored in the memory 502. The control module 59 is connected to the driving member 103 of the sample containing device 1 and configured to control the driving member 103 to drive the rotating member 101 rotate at a set angle $\alpha$ every set time T, so that the detector 3 performs multi-point detection on the ore sample to be detected to obtain an average value. For example, the set time T=60 s, the set angle $\alpha$=180°, the sample container 102 adopts a sample tray, and the control module 59 controls the driving member 103 to drive the sample tray rotate at 180° every 60 s according to the set time T, thus, the automatic control of multi-point measurement of the sample is realized. It is to be noted that the set time T and the set angle $\alpha$ can be set according to actual needs, and the set time T is not limited to 60 s and the set angle $\alpha$ is not limited to 180°.

In some embodiments, as shown in FIG. 11, the excitation unit 2 comprises:

a high-voltage power source 201, which is configured to output high-voltage power with different voltages; and a controllable X-ray excitation source 202, which is electrically connected to the high-voltage power source 201 and configured to output the X-rays with continuously adjustable energy according to the different voltages output by the high-voltage power source 201, so that the X-rays interact with the ore sample to be detected and excite the ore sample to generate the secondary X-rays.

In the above embodiments, the high-voltage power source 201 adopts a power source whose voltage is adjustable in a range of 0 kV to 50 kV; the controllable X-ray excitation source 202 adopts an X-ray excitation source whose input voltage and current are adjustable; and, the high-voltage power source 201 and the controllable X-ray excitation source 202 are the high-voltage power source and controllable X-ray excitation source known in the current market.

By adjusting high voltage, the controllable X-ray excitation source outputs the X-rays with continuously adjustable energy to excite the constituent elements in the ore sample, thereby multi-element measurement is realized.

In some embodiments, the detector 3 adopts a semiconductor detector with high energy resolution to realize the detection of the ore sample to be detected. Here, the high energy resolution means that the resolution at 5.9 keV is not less than 150 eV. Since the semiconductor detector has good energy resolution, with a half-maximum width of 140 eV (at 59 keV), it has a wider energy linear range; and, low temperature condition is obtained by electric refrigeration, which is easy to use compared with the conventional liquid nitrogen refrigeration detector. It is to be noted that the semiconductor detector used in these embodiments is the semiconductor detector known in the market.

Specifically, the detector 3 may be a SiC detector, a Si-PIN detector or a CdZnTe detector; wherein, the SiC and CdZnTe detectors are detectors made of SiC and CdZnTe materials respectively and can be used to detect X-rays, the Si-PIN detector is a detector with a PIN junction formed in a Si substrate and can be used to detect X-rays. It is to be noted that the specific structure of the detector 3 is not limited in the present application.

In some embodiments, referring to FIG. 1, the signal processing unit 4 comprises:
- a signal amplifier 401, which is connected to the detector 3 and configured to amplify and shape the secondary X-rays detected by the detector 3; and
- a multichannel pulse amplitude analyzer 402, which is connected to the signal amplifier 401 and configured to perform analog-to-digital conversion on amplified secondary X-rays and then perform classification to obtain the counts and the energy of the secondary X-rays.

Specifically, the signal amplifier and the multichannel pulse amplitude analyzer adopt the signal simplifier and multichannel pulse amplitude analyzer known in the current market.

When using the ore component analysis device provided by the aforementioned embodiments to analyze ore components, the specific operation principle is given below.

The high-voltage power source 201 outputs high voltage with different voltages, so that the controllable X-ray excitation source 202 outputs X-rays with continuously adjustable energy to the ore sample to be detected, and the X-rays with different energy interact with the ore sample to be detected and excite the ore sample to generate secondary X-rays with different energy. The detector 3 detects the secondary X-rays and transmits them to the signal simplifier 401, the signal amplifier 401 amplifies and shapes the detected secondary X-rays, and the multichannel pulse amplitude analyzer 402 performs analog-to-digital conversion and classification to obtain the count and the energy of the secondary X-rays with different energy. The matching module 52 matches the energy of the secondary X-rays with the energy of X-rays corresponding to the known elements stored in the storage module 51, and obtains the occurrence probability of the secondary X-rays and the corresponding elements according to the matched X-ray energy. The count correction module 53 corrects the counts of the secondary X-rays according to the attenuation efficiency of the secondary X-rays in the air, and the peak seeking module 54 seeks peaks on the corrected energy spectrum of the secondary X-rays and calculates the peak area of each peak. The calculation module 55 calculates the content $P_i$ of each element in the ore sample according to the peak area and the occurrence probability of the secondary X-rays. The content correction module 56 performs matrix effect correction on the calculated content of each element by using the measurement result of the standard ore sample to obtain the final content of each element in the ore sample. The display module 57 displays the analyzed elements in the ore and the content value of each element, and the Internet of Things module 58 transmits the analyzed elements in the ore and the content value of each element to the external data monitoring platform (e.g., our own cloud platform, a third-party platform, etc.). Thus, according to the component analysis result, the control of ore classification/desliming and other operations is realized, the current production mode of the ore processing industry is changed, and the production efficiency is improved.

In the ore component analysis device provided by the aforementioned embodiments, the count correction module 53 is provided to correct the counts of the secondary X-rays according to the attenuation efficiency of the X-rays in the air, and the content correction module 56 is provided to perform matrix effect correction on the calculated content of each element by using the measurement result of the standard ore sample, so that the analysis device can be directly used in the air without the control of the vacuum pump and can be directly applied to the production line, thus, the ore component analysis process is simplified, the manpower and time cost are saved and the production efficiency is greatly improved.

According to a second aspect of the embodiments of the present application, an ore component analysis method is provided, comprising the following step:

S1: X-rays with continuously adjustable energy are emitted to an ore sample to be detected, and the X-rays with different energy interact with the ore sample to be detected and excite the ore sample to generate secondary X-rays with different energy;

S2: the secondary X-rays are detected, and the secondary X-rays are amplified, shaped and classified to obtain counts and energy of the secondary X-rays with different energy;

S3: the energy of the secondary X-rays is matched with energy of X-rays corresponding to known elements (for example, referring to FIG. 3 which shows the energy of X-rays corresponding to some elements) to determine elements corresponding to the secondary X-rays and obtain occurrence probability of the secondary X-rays;

S4: the counts of the secondary X-rays is corrected according to attenuation efficiency of the secondary X-rays in the air to obtain a corrected energy spectrum of the secondary X-rays, peaks are sought on the corrected energy spectrum of the secondary X-rays, and peak area of each peak is calculated;

S5: content of each element in the ore sample is calculated according to the peak area and the occurrence probability of the secondary X-rays, where the content $P_i$ of an element i is expressed as:

$$P_i = \frac{I_i}{\sum I_i} = \frac{A_i/(\varepsilon_i \times \varepsilon_j)}{\sum A_i/(\varepsilon_i \times \varepsilon_j)}, \tag{1}$$

where $I_i$ is an intensity of the element i, $A_i$ is the peak area of the element i, $\varepsilon_i$ is the occurrence probability of the secondary X-rays of the element i, and $\varepsilon_j$ is intrinsic detection efficiency of the detector for the secondary X-rays of the element i and the content of each element is calculated according to the above formula; it is to be noted that the intrinsic detection efficiency of the detector is a known parameter of the detector.

S6: matrix effect correction is performed on the calculated content of each element by using a measurement result of a standard ore sample to obtain final content of each element in the ore sample.

An excitation unit 2 (e.g., a controllable X-ray excitation source, etc.) and a detector 3 (e.g., a semiconductor detector, etc.) are arranged above the ore sample to be detected. The X-rays are output by the excitation unit 2, and the secondary X-rays are detected by the detector 3. In some embodiments, an included angle formed by the excitation unit 2, the sample containing device 1 and the detector is 45° to 135°. Thus, on one hand, it can be ensured that the ore sample to be detected can be effectively excited by the X-rays; on the other hand, the excited secondary X-rays can be fully absorbed by the detector 3. It is to be noted that the included angle can be selected according to actual needs. For example, the included angle may be 45°, 135°, 60°, 90°, 120°, etc.

In some embodiments, a specific method of correcting the counts of the secondary X-rays is given as follows: assuming that the energy of the secondary X-rays is E, a corrected count of the secondary X-rays with energy of E is expressed as:

$$y = x/\varepsilon 1 \qquad (2),$$

where y denotes the corrected count of the secondary X-rays, x denotes a count of the secondary X-rays with energy of E, and ε1 denotes the attenuation efficiency of the secondary X-rays with energy of E in 1 cm air and can be measured by experiments.

In some embodiments, after peaks are sought on the corrected energy spectrum of the secondary X-rays, the peak area of each peak is calculated by integration. Since it is a known technology to calculate the peak area on the energy spectrum by integration, the specific process of calculating the peak area by integration will not be described in detail here.

In some embodiments, a specific step of performing matrix effect correction is given as follows: assuming that content of the element i in the standard ore sample is A and content of the element i in the standard ore sample calculated by the formula (1) is B, then the final content $P_{ALi}$ of the element i in the ore sample to be detected is:

$$P_{ALi} = \frac{P_i}{B/A}. \qquad (3)$$

For example, if a concentration of element potassium in the standard ore sample is 10% and a concentration of element potassium in the standard ore sample calculated by the calculation module is 15% which is 1.5 times of the real concentration, during the measurement of a non-standard sample, the final content of element potassium in the non-standard sample is obtained by dividing the calculated content $P_K$ by 1.5. If a concentration of element calcium in the standard ore sample is 10% and a concentration of element calcium in the standard ore sample calculated by the calculation module is 13% which is 1.3 times of the real concentration, during the measurement of a non-standard sample, the final content of element calcium in the non-standard sample is obtained by dividing the calculated content $P_{Ga}$ by 1.3.

In some embodiments, it is also possible realize multi-angle measurement (i. e., multi-point measurement) by changing an angle of the ore sample to be detected. Specifically, by rotating the sample container 102 with the ore sample to be detected placed therein, the ore sample also rotates together with the sample container 102, and multi-point measurement is performed on the ore sample to obtain an average value, so that the measurement deviation caused by uneven distribution of elements inside the sample is solved and the measurement result is more accurate. When the sample container 102 rotates, the rotation of the sample container 102 can be automatically controlled by driving the sample container 102 to rotate at a set angle α every set time T, thus, manpower cost is saved. For example, the set time T=60 s, the set angle α=180°, and the sample container 102 is driven to rotate at 180° every 60 s to realize the automatic control of multi-point measurement of the sample. It is to be noted that the set time T and the set angle α can be set according to actual needs, and the set time T is not limited to 60 s and the set angle α is not limited to 180°.

In some embodiments, after the step S6, the method further comprises a step S7: displaying the elements in the ore sample and the content of each element and uploading to an external data monitoring platform (e.g., our own cloud platform, a third-party platform, etc.). Thus, according to the component analysis result, the control of ore classification/desliming and other operations is realized, the current production mode of the ore processing industry is changed, and the production efficiency is improved.

In the ore component analysis method provided by the aforementioned embodiments, the count of the secondary X-rays is corrected according to the attenuation efficiency of the X-rays in the air, and matrix effect correction is performed on the calculated content of each element by using the measurement result of the standard ore sample, so that the analysis device can be directly used in the air without the control of the vacuum system and can be directly applied to the production line, thus, the ore component analysis process is simplified, the manpower and time cost are saved and the production efficiency is greatly improved.

The foregoing embodiments are used for explaining the present application, rather than limiting the present application. Any modifications and alterations made to the present application without departing from the spirit of the present application and the protection scope of the appended claims shall fall into the protection scope of the present application.

The invention claimed is:

1. An ore component analysis device, comprising:
a sample containing device, which is configured to place an ore sample to be detected;
an excitation unit, which is arranged above the sample containing device and configured to output X-rays with continuously adjustable energy, so that the X-rays interact with the ore sample to be detected and excite the ore sample to generate secondary X-rays;
a detector, which is arranged above the sample containing device and configured to detect the secondary X-rays;
a signal processing unit, which is connected to the detector and configured to amplify, shape and classify the secondary X-rays detected by the detector to obtain counts and energy of the secondary X-rays; and
a data processing device, which is connected to the signal processing unit and configured to analyze and calculate data processed by the signal processing unit, wherein the data processing device comprises a processor and a memory, and the processor is configured to execute following program modules stored in the memory:

a storage module, which is configured to store known elements and energy and occurrence probability of X-rays corresponding to the elements;

a matching module, which is configured to match the energy of the secondary X-rays with the energy of the X-rays corresponding to the known elements stored in the storage module so as to determine elements corresponding to the secondary X-rays and obtain occurrence probability of the secondary X-rays;

a count correction module, which is configured to correct the counts of the secondary X-rays according to attenuation efficiency of the secondary X-rays in the air to obtain a corrected energy spectrum of the secondary X-rays;

a peak seeking module, which seeks peaks on the corrected energy spectrum of the secondary X-rays and calculates peak area of each peak;

a calculation module, which calculates content of each element in the ore sample according to the peak area and the occurrence probability of the secondary X-rays, where the content $P_i$ of an element i is expressed as:

$$P_i = \frac{I_i}{\sum I_i} = \frac{A_i/(\varepsilon_i \times \varepsilon_j)}{\sum A_i/(\varepsilon_i \times \varepsilon_j)}, \quad (1)$$

where $I_i$ is an intensity of the element i, $A_i$ is the peak area of the element i, $\varepsilon_i$ is the occurrence probability of the secondary X-rays of the element i, and $\varepsilon_j$ is intrinsic detection efficiency of the detector for the secondary X-rays of the element i; and a content correction module, which is configured to perform matrix effect correction on the content of each element calculated by the calculation module by using a measurement result of a standard ore sample to obtain final content of each element in the ore sample.

2. The ore component analysis device according to claim 1, wherein an included angle formed by the excitation unit, the sample containing device and the detector is 45° to 135°.

3. The ore component analysis device according to claim 1, wherein the processor is further configured to execute a display module and an Internet of Things module stored in the memory; the display module and the Internet of Things module are connected to the content correction module, respectively; the display module is configured to display the final content of each element in the ore sample; and, the Internet of Things module is configured for connection to an external data monitoring platform.

4. The ore component analysis device according to claim 1, wherein the sample containing device comprises:

a rotating member, above which the excitation unit and the detector are located;

a sample container, which is placed in the rotating member and configured to place the ore sample to be detected; and a driving member, having an output shaft which is coupled to a bottom of the rotating member and configured to drive the rotating member to rotate.

5. The ore component analysis device according to claim 4, wherein the processor is further configured to execute a control module stored in the memory; the control module is connected to the driving member and configured to control the driving member to drive the rotating member rotate at a set angle $\alpha$ every set time T, so that the detector performs multi-point detection on the ore sample to be detected to obtain an average value.

6. The ore component analysis device according to claim 1, wherein the excitation unit comprises:

a high-voltage power source, which is configured to output high-voltage power with different voltages; and a controllable X-ray excitation source, which is electrically connected to the high-voltage power source and configured to output the X-rays with continuously adjustable energy according to the different voltages output by the high-voltage power source, so that the X-rays interact with the ore sample to be detected and excite the ore sample to generate the secondary X-rays.

7. The ore component analysis device according to claim 1, wherein the signal processing unit comprises:

a signal amplifier, which is connected to the detector and configured to amplify and shape the secondary X-rays detected by the detector; and a multichannel pulse amplitude analyzer, which is connected to the signal amplifier and configured to perform analog-to-digital conversion on amplified secondary X-rays and then perform classification to obtain the counts and the energy of the secondary X-rays.

8. The ore component analysis device according to claim 1, wherein a specific method of correcting the counts of the secondary X-rays by the count correction module is given as follows: assuming that the energy of the secondary X-rays is E, a corrected count of the secondary X-rays with energy of E is expressed as:

$$y = x/\varepsilon 1 \quad (2),$$

where y denotes the corrected count of the secondary X-rays, x denotes a count of the secondary X-rays with energy of E, and $\varepsilon 1$ denotes the attenuation efficiency of the secondary X-rays with energy of E in 1 cm air and measured by experiments.

9. The ore component analysis device according to claim 1, wherein a specific step of performing matrix effect correction by the content correction module is given as follows: assuming that content of the element i in the standard ore sample is A and content of the element i in the standard ore sample calculated by the calculation module is B, then the final content $P_{ALi}$ of the element i in the ore sample to be detected is:

$$P_{ALi} = \frac{P_i}{B/A}. \quad (3)$$

10. An ore component analysis method, which performs analysis by using the ore component analysis device according to claim 1, comprising following steps of:

S1: emitting X-rays with continuously adjustable energy to an ore sample to be detected, so that the X-rays with different energy interact with the ore sample to be detected and excite the ore sample to generate secondary X-rays with different energy;

S2: detecting the secondary X-rays, amplifying, shaping and classifying the secondary X-rays to obtain counts and energy of the secondary X-rays with different energy;

S3: matching the energy of the secondary X-rays with energy of X-rays corresponding to known elements to determine elements corresponding to the secondary X-rays and obtain occurrence probability of the secondary X-rays;

S4: correcting the counts of the secondary X-rays according to attenuation efficiency of the secondary X-rays in the air to obtain a corrected energy spectrum of the secondary X-rays, seeking peaks on the corrected energy spectrum of the secondary X-rays, and calculating peak area of each peak;

S5: calculating content of each element in the ore sample according to the peak area and the occurrence probability of the secondary X-rays, where the content $P_i$ of an element i is expressed as:

$$P_i = \frac{I_i}{\sum I_i} = \frac{A_i/(\varepsilon_i \times \varepsilon_j)}{\sum A_i/(\varepsilon_i \times \varepsilon_j)}, \quad (1)$$

where $I_i$ is an intensity of the element i, $A_i$ is the peak area of the element i, $\varepsilon_i$ is the occurrence probability of the secondary X-rays of the element i, and $\varepsilon_j$ is intrinsic detection efficiency of the detector for the secondary X-rays of the element i and the content of each element is calculated according to the above formula;

S6: performing matrix effect correction on the calculated content of each element by using a measurement result of a standard ore sample to obtain final content of each element in the ore sample.

11. The ore component analysis method according to claim 10, wherein an excitation unit and a detector are arranged above the ore sample to be detected; the X-rays are output by the excitation unit, and the secondary X-rays are detected by the detector; and, an included angle formed by the excitation unit, the sample containing device and the detector is 45° to 135°.

12. The ore component analysis method according to claim 10, wherein in the step S4, a specific method of correcting the counts of the secondary X-rays is given as follows: assuming that the energy of the secondary X-rays is E, a corrected count of the secondary X-rays with energy of E is expressed as:

$$y = x/\varepsilon 1 \quad (2),$$

where y denotes the corrected count of the secondary X-rays, x denotes a count of the secondary X-rays with energy of E, and ε1 denotes the attenuation efficiency of the secondary X-rays with energy of E in 1 cm air and measured by experiments.

13. The ore component analysis method according to claim 10, wherein a specific step of performing matrix effect correction is given as follows: assuming that content of the element i in the standard ore sample is A and content of the element i in the standard ore sample calculated by the formula (1) is B, then the final content $P_{ALi}$ of the element i in the ore sample to be detected is:

$$P_{ALi} = \frac{P_i}{B/A}. \quad (3)$$

14. The ore component analysis method according to claim 10, wherein in the step S1, multi-angle measurement of the ore sample is realized by changing an angle of the ore sample to be detected.

15. The ore component analysis method according to claim 10, wherein after the step S6, further comprises a step S7: displaying elements in the ore sample and the content of each element and uploading to an external data monitoring platform.

* * * * *